(12) United States Patent
Albes

(10) Patent No.: US 11,529,232 B2
(45) Date of Patent: Dec. 20, 2022

(54) DEVICE THAT CAN BE IMPLANTED IN A MINIMALLY INVASIVE MANNER AND MITRAL VALVE IMPLANT SYSTEM

(71) Applicant: Immanuel Albertinen Diakonie gGmbH, Hamburg (DE)

(72) Inventor: Johannes Albes, Berlin (DE)

(73) Assignee: Immanuel Diakonie GmbH, Berlin (DE)

( * ) Notice: Subject to any disclaimer, the term of this patent is extended or adjusted under 35 U.S.C. 154(b) by 173 days.

(21) Appl. No.: 16/498,589

(22) PCT Filed: Mar. 28, 2018

(86) PCT No.: PCT/EP2018/058026
§ 371 (c)(1),
(2) Date: Feb. 3, 2021

(87) PCT Pub. No.: WO2018/178208
PCT Pub. Date: Oct. 4, 2018

(65) Prior Publication Data
US 2021/0161662 A1   Jun. 3, 2021

(30) Foreign Application Priority Data

Mar. 28, 2017 (DE) .................... 102017002976.8

(51) Int. Cl.
*A61F 2/24* (2006.01)
(52) U.S. Cl.
CPC .......... *A61F 2/2445* (2013.01); *A61F 2/2466* (2013.01); *A61F 2220/0016* (2013.01)
(58) Field of Classification Search
CPC ..... A61F 2/2445; A61F 2/2448; A61F 2/2466
See application file for complete search history.

(56) References Cited

U.S. PATENT DOCUMENTS 8,926,696 B2    1/2015   Cabiri et al.
9,072,511 B2    7/2015   Tegzes
(Continued)

FOREIGN PATENT DOCUMENTS

WO    2010/073246 A2    7/2010
WO    2013/088327 A1    6/2013

OTHER PUBLICATIONS

International Search Report dated Jun. 27, 2018 issued in corresponding PCT/EP2018/058026 application (2 pages).

*Primary Examiner* — William H Matthews
(74) *Attorney, Agent, or Firm* — Millen, White, Zelano & Branigan, PC; Ryan Pool

(57) ABSTRACT

The invention relates in general to the field of heart surgery. In the surgical field, instruments are used in order to examine the interior of living organisms and/or to use for operative interventions. These also include implants for the production of the functionality of a heart. The invention relates to such an implantable device and a method for eliminating regurgitation in the area of the heart. The implantable device is an annuloplasty ring with a large number of tissue anchors. An unfolded annuloplasty ring is positioned in the cavity of a body element in order to constrict a bodily opening. Using the minimally-invasive technique, each tissue anchor of the annuloplasty ring is intravascularly inserted in advance into a precise position on the edge of the mitral valve annulus. The annuloplasty ring that is configured in the shape of an arc or circle is mounted and fastened to the thus anchored fastening means in order to influence in size and shape the septal and lateral annulus of the mitral valve and to close the gap between the anterior and posterior cusps in the valve.

6 Claims, 7 Drawing Sheets

(56) References Cited

U.S. PATENT DOCUMENTS

| | | |
|---|---|---|
| 9,713,530 B2 | 7/2017 | Cabiri et al. |
| 10,058,318 B2 | 8/2018 | Tegzes |
| 10,143,553 B2 | 12/2018 | Alon et al. |
| 10,206,776 B2 | 2/2019 | Alon |
| 10,357,364 B2 | 7/2019 | Alon |
| 2012/0136436 A1 | 5/2012 | Cabiri et al. |
| 2012/0245604 A1 | 9/2012 | Tegzes |
| 2014/0309730 A1* | 10/2014 | Alon .................... A61F 2/2445 623/2.11 |
| 2015/0105855 A1 | 4/2015 | Cabiri et al. |
| 2015/0223802 A1 | 8/2015 | Tegzes |
| 2016/0120645 A1 | 5/2016 | Alon |
| 2017/0367825 A1 | 12/2017 | Cabiri et al. |
| 2018/0256328 A1 | 9/2018 | Alon |
| 2019/0038411 A1 | 2/2019 | Alon |
| 2019/0053905 A1 | 2/2019 | Alon |
| 2019/0117397 A1 | 4/2019 | Alon |

* cited by examiner

DEVICE THAT CAN BE IMPLANTED IN A MINIMALLY INVASIVE MANNER AND MITRAL VALVE IMPLANT SYSTEM

This invention relates to a minimally-invasive implantable device and a mitral-valve-implant system.

BACKGROUND

Medicine is used to detect and eliminate diseases, with the purpose of restoring the health of patients. This disclosure relates to the field of heart surgery. In the heart-surgery field, instruments, devices or methods are used in order to examine the interior of the heart and/or to use surgical interventions. In particular, this invention relates to the minimally-invasive reconstruction of heart valves, whereby surgical instruments are used which, with access to the heart, allow various reconstructions and the insertion of inventive devices into beating hearts to be performed. The device is an implantable device for fastening to a tissue, by which an opening in the expansion is limited or constricted. This is an annuloplasty ring, which can be used in a cavity of a bodily organ, in particular in a heart, to correct a mitral valve insufficiency.

The heart is a muscular hollow organ, which pumps blood through the body with rhythmic contractions and thus ensures the supply to all organs. Heart disease can therefore lead to various functional disorders. For example, cardiac insufficiency is considered to be a functional disorder. Cardiac insufficiency is the pathological inability of the heart to convey the amount of blood required by the body without raising the pressure in the heart atria. Cardiac insufficiency is divided according to its course, according to the predominantly-affected half of the heart (right or left) and according to the mechanism. Another common disease of the heart is the heart valve defect. A heart valve defect is a functional disorder of one or more heart valves. A heart valve defect can affect each of the four heart valves, whereby the valves in the left heart, the aortic and mitral valves, are considerably more commonly affected than the valves of the right heart. The functional disorder can consist of a constriction (stenosis), an inability to close (insufficiency), or a combination of the two (combined heart defect).

The mitral valve acts as a non-return valve. The inability to close or the leak of the mitral valve of the heart during the discharge phase (systole) results in a proportional reflux of oxygenated blood from the left chamber of the heart (left ventricle) into the left atrium, while the bulk of the oxygenated blood is forced through the aortic valve into the aorta. Mitral valve regurgitation can develop from a large number of various mechanical defects in the mitral valve. The valve seal, the valve, the tendinous cords, which connect the valvular cusp to the papillary muscles, or the papillary muscles themselves can be damaged or can be dysfunctional in some other way. Usually, the valve ring can perform the function of adequately closing a mitral valve against the high pressure of the left ventricle. To avoid regurgitation of the valve, i.e., a reflux of blood from the left ventricle into the left atrium during a normal cycle of the cardiac contraction, various devices and methods for mitral valve reconstruction are known from the state of the art. Mitral valve reconstruction is the restoration of the valve function with preservation of the mitral valve. Surgical methods include, for example, sternotomy, and catheter-guided and minimally-invasive annuloplasty. As devices, annuloplasty rings of all types are used in order to eliminate leakage in the mitral valve between the posterior cusp (posterior leaflet) and the anterior cusp (anterior leaflet).

An abundance of various annuloplasty rings is known from the state of the art: for example, rigid, semi-rigid and flexible annuloplasty rings as well as closed, half-closed or open annuloplasty rings. Also, the shape of the annuloplasty ring is different and can be designed circular, D-shaped, C-shaped or kidney-shaped. Also, the materials of the annuloplasty rings are different. Some have all mechanical annuloplasty rings but commonly, they consist, on the one hand, of non-dissolvable material since they have to grow on the valve ring of the valvular cusp and, on the other hand, they should perform the function of the natural mitral valve.

For example, U.S. Pat. No. 8,545,414 B2 discloses such an annuloplasty ring. The annuloplasty ring comprises an inner material that consists of high-grade steel, e.g., titanium, or it consists of a flexible material, such as silicone rubber or Dacron. The inner material is covered by a surrounding material, such as biocompatible tissue or cloth. During the annuloplasty method, an annuloplasty ring is implanted in the mitral valve annulus in order to eliminate regurgitation. The annuloplasty ring is designed rod-shaped and has the shape of a capital "D." In the relatively straight section, it has an opening and consists of plastic with a DACRON meshwork covering.

This annuloplasty ring is attached to the anterior and posterior valve rings of the cusp. The drawback of this annuloplasty ring consists in the rigid and flat embodiment. Another drawback consists in the fact that it can be used only with the conventional sternotomy in the left atrium of the heart. Also, the type of fastening is disadvantageous. The fastening of the annuloplasty ring is done by attaching a through-going implant seam along the mitral valve on the valve ring. An unsuitable attachment in the anterior segment could, however, produce an undesirable intratrigonal shortening of the annulus.

Another annuloplasty ring for implantation on a mitral valve is disclosed in U.S. Pat. No. 6,858,039 B2. In contrast to the above-mentioned rigid and flat embodiment of an annuloplasty ring from U.S. Pat. No. 8,545,414 B2, this embodiment is designed semi-rigid. In addition, this annuloplasty ring has a shape change not only in the X-Y plane, but also in the Z-direction, ensuring that it comes significantly closer to the shape of the mitral annulus, which does not lie just in a flat plane. The annuloplasty ring must only preserve its rear bending against the stresses that are generated by the musculature of the heart during each stroke cycle. It therefore consists of a material such as Elgiloy (a cobalt-nickel-alloy), titanium or nitinol (a nickel-titanium alloy). The fastening of the closed annuloplasty ring, designed in approximately a D shape, is carried out by attachment. The ring encloses an inner ring element and an outer attaching sheath, which make it possible that the ring element can be attached in the mitral annulus. The attaching sheath is porous and flexible enough to make it possible for a thread to go through the ring. Also, this annuloplasty ring can be implanted in the heart only by applying the standard sternotomy. The attaching of an annuloplasty ring is carried out with a through-going implant seam along the mitral valve on the valve ring. An unsuitable attachment in the anterior segment could, however, produce an undesirable intratrigonal shortening of the annulus.

A further development of an annuloplasty ring can be deduced from EP 0 624 080 B 1. The annuloplasty ring has pull threads, by which it can be made smaller on the periphery. The pull threads are able to reduce the size of the posterior section of an annuloplasty ring. Therefore, EP 0

624 080 B1 calls for an annuloplasty ring that can still reduce a valve insufficiency after fastening by attaching spaced seams to the annulus. The reduction is done by tightening one or more pull threads, by which the periphery of the annulus can be further reduced in order to correct or to minimize residual valve insufficiency that remains after the ring implantation. The drawback of this annuloplasty ring consists in that it can be implanted in the heart only using the standard sternotomy. Only with eyes on the mitral valve is it possible to attach this annuloplasty ring, to tighten and to knot the pull threads appropriately. Typically, during surgery, the previously-shown annuloplasty rings are implanted in the open heart, in which an annuloplasty ring can be attached to the valve annulus. Open-heart surgery is a highly-invasive method, which requires a heart-lung machine.

To avoid a sternotomy, U.S. Pat. No. 9,433,503 B2 therefore proposes a segmented annuloplasty ring, which is configured in its embodiment in such a way that it can be fed to the heart by a catheter, using, for example, a transseptal attachment or a transapical attachment. The above-mentioned rigid and/or semi-rigid annuloplasty rings are not suitable to be able to be introduced into a heart by a catheter. The annuloplasty ring in question comprises an outer hollow element with a large number of movable segments. Adjacent segments interact with one another in a rotational movement in a limited angular range. This disclosure represents systems and methods for the repair of heart valves. This takes place by a percutaneous transcatheter dispensing and fixing of an annuloplasty ring on the heart valves. The embodiments of the annuloplasty rings are designed in an elongate introductory geometry for the feeding catheter. Based on the elongate embodiment, an annuloplasty ring can be fed by a catheter for implantation on a valve ring. The feeding of the catheter to the heart is done, e.g., via the inguinal access and the attached vena cava, e.g., via the inferior vena cava into the right atrium, via the interatrial septum into the left atrium; the annuloplasty ring is then positioned there on the valve ring. The positioning is reviewed using ultrasound, fluoroscopy, i.a., imaging methods. During the review, the two free ends of the annuloplasty ring are then connected to one another via a pull tab. The segmented annuloplasty ring, on which segments a large number of spaced anchors are arranged, then has a geometric "D shape." The anchors are curved and are driven into the tissue via a balloon. An additional attachment of the anchors is not necessary. Such an annuloplasty ring consists of biological or biocompatible material and contains a nitinol rod in the interior. The drawbacks of this annuloplasty ring are the complicated method of the implantation by a catheter and the fastening of the anchors, as well as the change in size and shape of the annuloplasty ring on the valve ring, not described in more detail, in order to completely eliminate regurgitation.

Another relatively elastic annuloplasty ring as an implant on an annulus of a mitral valve can be deduced from U.S. Pat. No. 8,945,210 B2. This implant is inserted into the heart through a myocardial section, whereby the implant is already complete during insertion through the opening into the atrium. The implant is detachably fastened to an adjusting tool and is guided from the latter to the annulus of the mitral valve. Based on its flexibility, the implant can be matched to the size and shape of the annulus. At the places provided on the implant, the latter is then attached to the annulus through the open surgical incision in the heart. Subsequently, the incision in the heart is closed again, whereby the adjusting tool still remains on the implant. As soon as the patient is "off pump" again and there is a normal blood flow through the heart, additional adaptations to the size of the implant can be carried out, if necessary. An adaptation is carried out by manipulating the adjusting tool, which, e.g., actuates a gear rack system in the circular implant. A drawback of this embodiment of the annuloplasty ring is that the latter cannot be implanted in the beating heart.

To repair heart valves, U.S. Pat. No. 8,470,028 B2 discloses devices as implants. An implant relates to a valve for eliminating mitral valve regurgitation. The valve is inserted between the valve leaflets of the mitral valve. Another device relates to an additional implant that is designed as a stent. The flexible stent is fed to the mitral annulus percutaneously, as a prestressed implant, via a supply catheter that can be directed through the inguinal artery and the interatrial septum. At the site of the annulus, the retracted stent is opened and matched to the latter. For attachment to the annulus, the stent has fastening means, such as prongs, hooks, i.a. In addition, the circular stent can be equipped with spaced magnets. It has proven to be a drawback that the widening and placing, i.e., the matching of the stent to the size and shape of the mitral annulus, is subject to problems and therefore could not pass through this implant during heart surgery. In addition, the drawbacks of the catheter that is guided via the inguinal artery are to be avoided.

U.S. Pat. No. 9,072,511 B2 disclosed an annuloplasty ring or its fastening with a tissue anchor. Also, this annuloplasty ring that is designed "C-shaped" in the normal case is fed into the left atrium via a catheter for implanting in the mitral valve ring. For implanting, it is necessary to deploy, to position and to fasten the annuloplasty ring in the left atrium using the catheter. The fastening is done with three or four spiral tissue anchors, whereby a large number of various anchorings can be used. The annuloplasty ring is referred to as an implant element and normally consists of three or four arc-shaped segments. The number of segments is determined by the size of the valve, the size of the elongated segments and by the catheter volume. The segments are connected to one another via hinges and can embody a defined, but limited, pivoting movement. The pivoting movement can also be carried out via bending joints that are provided. The implant element then consists of an individual piece of material. In principle, such an annuloplasty ring has a rigid structure, however, which is produced from the segments. To avoid repetitions, reference is made to the previously-cited drawbacks of a rigid structure (excessive bending stiffness; insufficient matching to the shape of a valve ring; after attachment or anchoring, the occurrence of various stresses on the valve ring, etc.). Only with the additional insertion of a crossbar into the "C-shaped" implant element can a D-shaped structure be achieved for an annuloplasty ring. For attachment of an implant element that consists of three segments, first three or four individual tissue anchors are inserted into the heart tissue around the valve ring. The tissue anchors are fastened with guide wires in the provided clearance holes to the segments of the implant elements and generate stress on the rigid implant element and on the tissue of the mitral valve annulus. The fastening of a guide wire on the implant element is done using fastening elements. The embodiment of the segmented annuloplasty ring from U.S. Pat. No. 9,072,511 B2 is fastened to the implanted spiral tissue anchors.

The tissue anchors are advanced up to the left atrium in a catheter sleeve. The places at which the tissue anchors are to be placed were first determined with an anchor guide frame and lie on a circle in the mitral annulus. For centering the anchor guide frame, a fin is inserted into the valve gap of the mitral valve. In another method, a localization part of the anchor guide frame is mounted on the mitral valve. Subsequently, the anchor guide frame is opened, and its arm for positioning the tissue anchor is removed. The implantation method thus comprises the placing of the tissue anchors via an anchor guide frame onto selected sites in an atrium of a mitral valve of a left atrium of a heart. Attachment of an implant element to the annulus is then done on the embedded tissue anchors. Since the tissue anchors are provided with guide wires, which reach to outside of the body, the segments of the implant element are pushed onto these free ends, advanced by the catheter sleeve and placed on the tissue anchors. To this end, the segments of the implant element contain openings that are moved over the ends of the tissue anchors. For guiding the ends of the tissue anchors, a first conical sleeve is moved onto the end of a tissue anchor. The conical counterpart is also once more a sleeve or a conical opening in the segment. If the counterpart is a second sleeve, the latter is moved over the first sleeve, whereby the two sleeves are then located in the pivot joint of two segments. Another cylindrical compression spring is also arranged above the sleeves. For fastening a tissue anchor onto the segment of an implant element, the end of the tissue anchor has an annular groove. After a segment is placed on a tissue anchor, the annular groove is located above the fastening opening of the segment and above the compression spring. A clamping element that is also fed via the guide wire is also arranged via the compression spring. The clamping element can consist of, for example, a lock washer, with which a segment of the implant element is connected to a tissue anchor. This fastening process of the segments is repeated on all embedded tissue anchors. Because of the large number of individual parts for fastening an annuloplasty ring to the tissue anchors, a drawback develops during implantation. Another drawback is that the deformed shape of the left ventricle, which leads to constraints when the mitral valve is closed, cannot be restored with the above-mentioned implant elements in order to achieve an optimal valve closure. Remodeling of the mitral annulus cannot be adequately achieved with rigid and semi-rigid annuloplasty rings. Also, the method that is used for implantation of a rigid annuloplasty ring, with catheter-guided support, has drawbacks, as previously indicated. Catheters have a great deal of lengthwise capacity specifically in the longitudinal direction, but only slight capacity in the lateral or radial direction. The lumen of a catheter is limited because of the access paths to the heart.

The surgical restoration of a mitral valve has been further developed over recent decades. In order to pursue this change to the mitral valve repair and to make available new advances with alternative and additional devices and other surgical methods, it is necessary to avoid the above-mentioned drawbacks of the annuloplasty rings and primarily their implantation methods. Diseased mitral valves were previously conventionally operated via the access to the open ribcage so that open-heart surgeries could be pursued; see the previously-indicated state of the art and FIG. 1. If this intervention were associated with a patient with too high a risk, the intervention would be performed using a catheter. In this case, the annuloplasty ring with a thin sleeve is moved through the vessels into the heart; see the previously-indicated state of the art and FIG. 2. The two methods of sternotomy, which require an incision in the middle of the chest and the medical method in which access to the internal organs is achieved via a catheter-guided intervention (transcatheter technology), e.g., via the inguinal artery, are therefore not to be applied. In addition, it is necessary at least not to use rigid designs for annuloplasty rings. Also, the annuloplasty rings should make possible a simple fastening to beating hearts. The fastening of an annuloplasty ring is to occur without attaching to the mitral valve annulus, and there is to be a reduction in the number of technical components in the case of the rigid and membered annuloplasty rings that consist of segments.

Today, various conventional and minimally-invasive surgical methods are used in heart valve interventions. Heart valve interventions are catheter-supported and/or surgical interventions on heart valves or heart valve cusps, with the purpose of restoring the functionality of a heart valve. For the production of functionality, various technical methods and surgical instruments are thus available. Such techniques comprise the repair and the replacement of heart valves. In order to be able to conduct a repair on the heart, there are various access paths. A surgical access path to the heart is carried out by, for example, the thoracotomy in the form of a median sternotomy, which enables access in the patient's chest cavity. To this end, the sternum must be cut open or sawed open according to the length. With a rib spreader, the two halves of the ribcage are then stretched from one another. The surgical team now gains a clear view of the heart and the thoracic vascular systems. Because of the good visualization and size of the operating field, a large number of surgical instruments can be used. In a patient, such an opening of the ribcage, however, causes a high degree of traumatization, extended stays in the hospital and an extended healing process. This known access method and the surgical instruments that are used in this respect are only shown here to document the state of the art.

In many heart diseases, such as in, e.g., cardiac insufficiency, the intervention on the heart is performed using catheters. The transcatheter technology as access to the heart has to a large extent replaced thoracotomy in some areas. Many heart valve defects can be corrected in a gentle way by modern catheter methods, which can occasionally prevent a more major operation. In particular, in this day and age, defects of the heart valves of the left half of the heart, i.e., of the aortic valve and mitral valve, are treated using a catheter. As also in the case of other catheter interventions, a plastic catheter is advanced via a blood vessel into the groin or into the arm up to the heart. Also, this access method (transcatheter technology) to the heart is only shown here in order to document the state of the art.

For a large number of heart diseases or cardiac insufficiencies, access to the heart is carried out using the minimally-invasive method, in particular in the case of mitral valve surgery. In the case of mitral valve surgery, the opening of the ribcage of a patient and the use of a heart-lung machine were previously still necessary.

The proportion of minimally-invasive surgery continuously increases in the elimination of mitral valve insufficiencies in the heart and increasingly triggers the other surgical methods, such as sternotomy technology and the technically-challenging transcatheter technology. The surgical path is moving away from open-heart surgery to the application of minimally-invasive surgery.

In the case of mitral valve reconstruction, it is necessary to change the state of the art with the application of minimally-invasive surgery in such a way that the minimally-invasive intervention can be carried out in the case of the implantation of an annuloplasty ring in beating hearts in order to eliminate regurgitation. That is to say, devices and methods are to be developed in such a way that open-heart surgery for the reconstruction of mitral valves is no longer necessary. Surgery is moving away from open-heart surgery and toward minimally-invasive surgery.

A distinction is still to be made between an aortic valve reconstruction and a mitral valve reconstruction. The mitral valve reconstruction is a restoration of the valve function with preservation of the mitral valve (bicuspid valve). For successful repair of the valve function of a mitral valve in the interior of a human heart, the various components of the mitral valve are therefore to be studied and their possible defects are to be verified. The study is done, i.a., using diagnostics before and during surgery, e.g., with an angiography that is supported by contrast media, x-ray fluoroscopy and transthoracic and transesophageal echocardiography. Only the use and advances in diagnostics make it possible to be able to perform operations on beating hearts with minimally-invasive surgery.

According to the state of the art, a mitral valve reconstruction is carried out in principle as follows: preliminary testing, e.g., with EKG, echocardiogram (TEE), transesophageal ultrasound (ultrasound probe), heart catheter, Doppler study, lung function test and investigation of the size of the annulus (diameter of the mitral valve) to determine the valve ring implant that is to be inserted, narcotization of the patient, approximately 3-cm incision in the groin area, connection to the heart-lung machine, connection for a contrast medium, positioning of an invasive access through an approximately 5- to 8-cm incision in the right pectoral muscle between the $4^{th}$ or $5^{th}$ rib, shutdown of the heart, use of endoscopy and additional imaging methods, opening of the left atrium with a small incision, putting artificial threads on the annulus, introducing the ring implant, attaching, knotting and cutting the threads on the ring implant, closing the left atrium, and closing the access on the ribcage, and the function of the mitral valve is reviewed directly after the surgery by a transesophageal ultrasound. It is necessary to avoid the connection of the heart-lung machine and the shutdown of the heart in the case of the implantation of ring implants in the heart and to attach them to the mitral annulus.

In order to meet the requirements imposed by minimally-invasive surgery on the heart valve implants, in particular on the annuloplasty rings and related surgical instruments, it is necessary to develop new embodiments of heart valve implants and surgical instruments.

The so-called seamless implantation of an annuloplasty ring by means of minimally-invasive surgery on beating hearts is known. The method of the minimally-invasive surgery has advantages in comparison to the other previously-mentioned methods, for example lower costs because of the shorter operating time, smaller surgical incisions and faster recovery of the patients. That is to say, in the case of percutaneous surgeries, the patients benefit by the reduction in surgical risk, the reduction of complications, and the shortening of stays. However, the use of the minimally-invasive technique also generates some special challenges. It must be possible to insert and fasten an annuloplasty ring via narrow tubes, meaning that the requirement regarding the complexity of the device structure could be increased since there is no direct visual contact with the annuloplasty ring to be implanted. On the one hand, such an annuloplasty ring must therefore be able to be compressed or pressed together in order to be moved through an access sleeve, which leads to the heart. In addition, the annuloplasty ring can be easily guided into the access sleeve and must not be squashed. On the other hand, the annuloplasty ring must expand itself in its original shape without additional help in order to be able to easily mount the fastening means that are implanted on the annulus of the mitral valve. In addition, the annuloplasty ring must be suitable for constricting tissue, e.g., a mitral valve ring or a bodily opening, e.g., an atrium. Therefore, an annuloplasty ring is equipped with simple but effective fastening means. That is to say, the traditional heart valve surgery and the minimally-invasive heart surgery are to be advantageously expanded here with another minimally-invasive surgical method. The guiding, placing and fastening of an annuloplasty ring as well as the positioning of the surgical instruments are therefore of special importance. Other important criteria are primarily the design of the implant and the instruments, since the design has a major influence on the handling during surgery without visual contact. That is to say, a large number of factors have to be considered in order to be able to perform a suitable operation for mitral valve reconstruction in a minimally-invasive manner: the age and general health of the patient, the extent of the damage to the valve, the type of valve and the preference of the patient.

Additional factors, which are cited below, are to be taken into consideration. In principle, the mitral valve reconstruction by application of annuloplasty has led to significant improvements in the case of mitral valve insufficiency. The purpose of the mitral valve annuloplasty is to restore the mitral valve competency, e.g., in the case of leaky mitral valves, by reconstruction of the physiological shape and function of the normal mitral valves. Under normal conditions, in the entire heart cycle, the mitral valves are subject to considerable dynamic changes in shape and size. These changes are primarily to be attributed to the dynamic movement of the surrounding mitral valve ring. During the cardiac cycle, the left atrium undergoes a sphincter movement and constricts the opening area during the systole in order to facilitate the coupling of the two cusps and to widen during the diastole in order to make possible a simple diastolic filling of the left atrium. This movement is further reinforced by a pronounced three-dimensional configuration, the characteristic saddle shape of the annulus, during the systole. The changes during the entire cycle are considered to be key for optimizing valve coaptation and for minimizing tissue stresses. The challenge of the mitral valve annuloplasty consists in improving the diseased and/or deformed shape of the mitral valve annulus and in restoring the physiological configuration and in this case in achieving normal ring dynamics. The annuloplasty enlarges the coaptation surface of the mitral cusp and thus reduces the tension forces that act on the reconstructed segments of the mitral valves. It is due to the role of the annuloplasty that a normal ratio between valve cusp surfaces and the annular surface is ensured in order to restore physiological coaptation. Annuloplasty is thus an efficient technique and in patients leads to good results. The inventive annuloplasty ring and its type of fastening meet these requirements and simplify, moreover, the implantation in beating hearts.

Heart surgeries can now select from a large number of various annuloplasty rings for restoring the original shape of a mitral valve annulus. The discussion in the case of the selection of the type, the size, the material and the shape of an annuloplasty ring that is to be inserted remains controversial. The material property of the annuloplasty rings can be of the flexible, semi-rigid or rigid type and incomplete or complete, planar or saddle-shaped, adjustable or non-adjustable in shape. As shapes, "C-shaped," "D-shaped," "circular," "kidney-shaped" and "saddle-shaped" annuloplasty rings are known. The surgeon determines the suitable size of an annuloplasty ring before implantation. The purpose is the reconfiguration of the length and shape of the mitral valve annulus and thus the mitral valve space or annular space. The material in the case of the annuloplasty rings can consist of, for example, a titanium alloy and the near-ring edge of a layer of silicone rubber, or the annuloplasty ring is produced with layers of Elgiloy and plastic strips and in turn is coated with silicone rubber on the near-line edge, or the inner core of an annuloplasty ring consists of a proprietary metal alloy or polyethylene or has a cell structure design that is able to simulate the physiological 3D movement of the native mitral valve ring and to take into consideration the anatomical saddle shape. Here, e.g., a shape memory alloy, such as nitinol, is considered. The core is frequently covered with tissue, which consists of, e.g., knit PET and is coated with carbon film or consists of knit PTFE, which contains one or more radiopaque, barium-impregnated silicon markers. In the case of the rigid embodiments of annuloplasty rings, the core consists of, i.a., rigid titanium wire, which is covered with highly-flexible PTFE tubing, polyester knit material and thin PTFE sleeves. If the annuloplasty ring consists exclusively of PTFE and a polyester seam, this ring is fully flexible and ensures that the valve ring moves. Most annuloplasty rings can have markers that contain barium-impregnated silicon, in order to make possible a radiological visualization. and thus can better perform the positioning of an annuloplasty ring.

SUMMARY

The object of the invention is to indicate a mitral valve implant, in particular an annuloplasty ring, which can be introduced within the framework of the application of minimally-invasive surgery via the right thoracic area and the left atrium of the heart and can be anchored there. An implant can therefore take on only the size that can be guided by a trocar and/or catheter to the surgical site.

Another object consists in equipping the implant with a fastening means. Multiple fastening means are to connect an annuloplasty ring to the threads of multiple implanted tissue anchors.

The device can be used for the use of minimally-invasive surgery on beating hearts. The device is inserted into an anatomical opening or another lumen, preferably on a mitral valve annulus for adjusting the shape and size of an anatomical opening. The annuloplasty ring of the device can be deformed from an original configuration into a guiding configuration and subsequently into an expanded configuration. In the starting position, the annuloplasty ring has its preselected, e.g., oval, embodiment. In its oval open form, the annuloplasty ring is pulled onto the threads of the tissue anchor. If all threads of the implanted tissue anchor are drawn through the annuloplasty ring, it is then pressed together to a specific size, by which it obtains its guiding configuration. In the compressed state, the annuloplasty ring is inserted into a sleeve of a surgical instrument, in which it is introduced compressed into the left atrium. In the atrium, the compressed annuloplasty ring is unfolded into an open configuration. The open shape of the annuloplasty ring corresponds to the original starting shape before the compression. At the site of the mitral valve annulus, the expanded annuloplasty ring with its original starting shape is put onto the implanted tissue anchor for influencing the geometry of the anatomical opening. Then, the annuloplasty ring is fastened to the implanted tissue anchors.

An implantable device is provided, which device can be inserted into beating hearts with a minimally-invasive technique and with access from the right side of the chest. A mitral valve implant is created, in particular for an annuloplasty ring, which is simple and economical in production and, on the other hand, an ergonomic method with implanting with simple handling is made possible. The device can be used for surgical restoration and better functionality of the mitral valve.

Different shapes and material properties for the annuloplasty rings naturally produce different effects on the mitral annulus and thus affect the functionality and closing ability of the valve of a mitral valve differently. Therefore, this disclosure is not limited to one embodiment or one special annuloplasty ring, but rather allows a large number of different material properties and differently-formed annuloplasty rings, which are suitable to be able to fasten to tissue anchors. This is made possible with the device, in particular with an annuloplasty ring, which is equipped at least with a tissue anchor, preferably with five or more tissue anchors. The number of tissue anchors that are to be implanted depends upon the size or the diameter of the mitral valve annulus in order to influence the shape and size of the mitral valve annulus positively and to eliminate regurgitation of the blood.

A tissue anchor can be provided. The tissue anchor can have a spiral-shaped coil screw and a plastic thread or can consist thereof. Such a tissue anchor can be introduced with the same surgical instrument into the tissue around the mitral valve annulus. A needle can also be arranged on the free end of the plastic thread of a tissue anchor. Further information regarding the needle is also given below. The tissue anchors can be introduced individually from the right side of the chest, in the left atrium, and can be implanted around the mitral valve annulus. Advantageously, approximately eight to ten tissue anchors are placed for receiving and fastening an annuloplasty ring. Advantageously, each free end of a plastic thread of the implanted tissue anchor is located outside of the thoracic space and is thus accessible to the surgeon. Each plastic thread can have a marking on the free end. The marking can be of the color type and/or can consist of an indicator or the like. Based on the marking, this shows at which site the related tissue anchor of the marked plastic thread on the mitral valve annulus is positioned. The positioning of the tissue anchors around the mitral valve annulus is shown in the example of FIG. 1.

In FIG. 2, an annuloplasty ring, which is attached around a mitral valve annulus, and the two cusps of the mitral valve are shown in a top view. The mitral valve annulus has an oval shape, which is designed approximately "D-shaped." The anterior cusp AL forms in the area of the annulus a relatively straight section relative to a curved posterior section of the posterior cusp PL. Since the path length of the relatively straight section is shorter than the path length of the curved section, three tissue anchors are advantageously arranged on the straight section, and five tissue anchors are arranged on the curved section. Distances between the tissue anchors can be the same or else different because of the anatomical 3D forming of the annulus. If, for example, as shown in FIG. 1, eight tissue anchors are implanted, eight threads are also located outside of the ribcage. Because of the marking on the threads, each thread that lies outside of the ribcage can be assigned to a tissue anchor that is implanted in the heart and to its position. The assignment of a thread and the position of its related tissue anchor is advantageously carried out in that an image structure is specified for the annulus in top view. The image structure provides the positions of the tissue anchors that are to be implanted. A marking is assigned to each position, for example with simple identification numbers or the like. The first implanted tissue anchor contains, e.g., the identification number 1, whereby a first position for implanting is specified in the tissue anchor. The first position of a tissue anchor on the annulus can, after it is first attached, be the left transition between the curved section and the straight section. In clockwise direction, the additional tissue anchors are then implanted. That is to say, the second tissue anchor that follows the first set tissue anchor receives the identification number 2 and is implanted in the specified position 2, etc. Naturally, the tissue anchors can also be implanted in another series. If, e.g., the first tissue anchor is implanted in the position 1, then the next tissue anchor is implanted in the position 3, whereby this tissue anchor naturally receives the identification number 3 and the subsequent tissue anchor that is to be implanted comes to the position 5 with the marking of the identification number 5 on the threads, etc. Also, the implanting of tissue anchors in another series is possible. It is important to note that when a tissue anchor is implanted in a preset position, the tissue anchor or threads thereof is provided with the corresponding positional data.

The implantation method thus comprises the placing of the tissue anchors at selected sites around the mitral valve annulus in the left atrium of a heart and the fastening of tissue anchors by screwing-in on the mitral valve annulus, by which the latter is surrounded with embedded tissue anchors. The placing and the implanting of the tissue anchors are supported by a large number of possible imaging measuring methods. For example, by using magnetic resonance imaging (MRI), intracardial echocardiography (ICE), transesophageal echography (TEE), fluoroscopy, CT scanning, endoscopy, intravascular ultrasound (IVUS) and/or other imaging, the mitral valve surgery or the implantation of the inventive device is tracked during the entire minimally-invasive method while various surgical instruments are being guided and/or while tissue anchors are being arranged for the precise placing and embedding of the tissue anchors to be implanted. For example, the TEE technique for determining the position of a tissue anchor to be implanted can be used.

If all tissue anchors are implanted around the mitral valve annulus, an annuloplasty ring is introduced with the corresponding surgical instrument. Ultrasound imaging can be used before the medical intervention in order to determine the size of the mitral valve annulus. Such information can be used in the selection of an appropriately set annuloplasty ring. In some cases, the annuloplasty ring can also be selected on the basis of the actual positions of the implanted tissue anchors.

First, the individual threads, on whose free ends a needle is located in each case, are guided through the fibrous ring, e.g., consisting of PET or PTFE tissue of an annuloplasty ring. To position a thread on the annuloplasty ring, it is necessary to use the same position at which the tissue anchor on the annulus is positioned. Therefore, seen in top view, the annuloplasty ring that is to be implanted with respect to the positioning in the tissue anchors has the same image structure as the image structure of the mitral valve annulus. In order to continue on with the previous example of the tissue anchor positions, the first tissue anchor is located at the first position, at the left transition between the curved section and the straight section of the annulus. The thread that is related to this tissue anchor 1 bears the identification number 1. This means that the thread 1 of the tissue anchor 1 at the corresponding point 1 has to be run through into the annuloplasty ring. That is to say, in order to be able to place the annuloplasty ring in the proper shape on the tissue anchors of the annulus, it is necessary to assign the identification number 1 to the thread and the position 1 of the tissue anchor to position 1 on the annuloplasty ring and to guide this thread at this point through the tissue of the annuloplasty ring. The position 1 on the annuloplasty ring also corresponds to the first position at the left transition between the curved section and the straight section of the annuloplasty ring. The first position on the annuloplasty ring corresponds to the first position of the implanted tissue anchor. The same applies for the other threads, which are provided by the tissue anchors and are now drawn to the corresponding positions by the tissue of the annuloplasty ring. That is to say, the thread 3 of the implanted tissue anchor 3, which is located at the position 3 on the annulus, is run through at the position 3 of the annuloplasty ring, whereby the position 3 on the annulus is identical to the position 3 on the annuloplasty ring. The thread 5 of the implanted tissue anchor 5, which is located at the position 5 on the mitral valve annulus, is run through to the position 5 of the annuloplasty ring, etc. Thus, it is ensured that the shape of an annuloplasty ring can be appropriately adapted to the shape of a mitral valve annulus and fastened to the tissue anchors. The positions on the annuloplasty ring, at which a thread can be pushed through in each case, can be position markers already marked out on the annuloplasty ring. If an annuloplasty ring is pulled onto all threads that are provided by the tissue anchors, the latter is advanced onto the threads up to a receiving surgical instrument.

An annuloplasty ring can be made of a deformable material that can be deformed manually. The deformation relates to a compression of the, e.g., oval shape of the annuloplasty ring to a minimum. The minimum of the shape with regard to geometry is achieved when the relatively straight anterior section has come as close as possible to the curved posterior section and two adjacent constrictions are formed. The diameter of such an annuloplasty ring is then compressed to a minimum of a few millimeters. The diameter then corresponds somewhat more than two times a cross-section of an annuloplasty ring. Based on the available lumen for the guiding configuration of the annuloplasty ring, it is not necessary to compress the annuloplasty ring to its minimum. The length of the annuloplasty ring in the compressed state has no influence when it is being guided to the site of the implantation in the atrium. If the tissue anchor threads are drawn through the starting shape of an annuloplasty ring, the latter are then pressed together or compressed. This compressed state of the annuloplasty ring is referred to as a guiding configuration. In the guiding configuration, the annuloplasty ring is inserted into a sleeve. The sleeve, which is guided through a trocar, reaches up into the left atrium of the heart.

With another surgical instrument, the annuloplasty ring is then moved from the sleeve, while the tissue anchor threads remain in addition outside of the body. If the annuloplasty ring exits from the sleeve and enters into the left atrium, it thus expands from its guiding configuration into its original starting shape. The original starting shape corresponds to the open oval configuration, whereby the annuloplasty ring is also always guided by the threads of the tissue anchors. Along the threads, the annuloplasty ring is now moved to the ends of the tissue anchors and placed there, whereby as previously described, it is fastened in the proper shape to the mitral valve annulus on the tissue anchor. Also, in the case of the manufacturing of tissue anchors with an annuloplasty ring, the TEE technique can be used, as well as the stopping of the fastening means on the threads of an annuloplasty ring.

The fastening of an annuloplasty ring to the tissue anchors can be carried out by a known method, such as suturing, knotting, etc. Simple fastening means for fastening an annuloplasty ring to the tissue anchors can be used. Advantageously, these fastening means are mounted on the tissue anchor threads that lie outside of the body and are advanced up to the annuloplasty ring. If the fastening means, which can clamp a tissue anchor thread, are placed on the annuloplasty ring in the area of the tissue anchor, they are cut away in the area of the fastening means and optionally knotted. The threads of the tissue anchors that are cut away are removed from the atrium and thus from the heart, and the incision in the heart wall is closed. Thus, the implantation of the inventive device, with the reference "MitraRing," is enclosed in the beating heart with use of minimally-invasive surgery, and regurgitation is eliminated. The mitral valve again performs its normal function and prevents the undesirable flowing-back of blood from the left ventricle into the left atrium, since the normal geometry of the mitral valve was restored. The mitral valve cusps again perform their valve function by better contact with one another. This is successfully achieved by the implantation of the inventive device, configured in a circular manner, on the mitral valve annulus. This form of the mitral valve surgery requires a minimally-invasive attempt to avoid a chest wall incision, a cardiopulmonary bypass and a heart and lung shutdown. Such a method is essentially more economical, does not require as much time and is associated with a low mortality risk for the patients.

The device is equipped with functions for the percutaneous introduction and change in shape of a mitral valve annulus and the application of the superior method of minimally-invasive surgery for constricting tissue or a bodily opening, such as a mitral valve, a tricuspid valve or an aortic valve, by means of such a device. In the minimally-invasive method, the device makes possible the implantation of an annuloplasty ring with the related tissue anchors and fastening agents in the tissue around the opening of an annulus. In this description, reference is made to heart surgery. The described method and the device can also be used in other operations in which tissue is to be tightened, such as, e.g., in gastric surgery or intestinal surgery.

The implant can have individual elements that, combined with one another, produce the mitral valve implant with the designation "MitraRing." The "MitraRing" is mainly formed from three elements. A first element is a spiral anchoring element, which consists of a coil screw with artificial threads. The second element is a flexible annuloplasty ring, which is fastened to multiple tissue anchors. The third element relates to a fastening means, in order to connect the annuloplasty ring to the tissue anchors. All three elements can be connected to one another to form a mitral valve implant after the manufacturing. A system is available for the method for implantation of such a device.

The system has a mitral valve implant, which is suitable for minimally-invasive repair of a mitral valve annulus in the beating heart of a patient. It has an outer tube spacer I, in particular an access cannula with lumen, for guiding an inner tube spacer II and a first inner tube spacer II, in particular a surgical instrument with lumen, for guiding and screwing-in a tissue anchor. After the implantation of the tissue anchor has taken place, the tube spacer II is exchanged for a second inner tube spacer III, in particular a surgical instrument with lumen, for guiding an annuloplasty ring. In this tube spacer III, a third inner tube spacer IV, in particular a surgical instrument with lumen, is inserted for receiving tissue anchor threads and for pushing the annuloplasty ring out of the tube spacer III until the annuloplasty ring is expanded in the atrium. Then, the tube spacers III and IV are removed and replaced by a fourth inner tube spacer V. The fourth inner tube spacer V, in particular a surgical instrument with lumen for guiding a fastening means, in particular a clamping means, is guided along a tissue anchor thread for fastening an annuloplasty ring.

DESCRIPTION OF THE EMBODIMENTS

Below, additional embodiments are explained in more detail with reference to the figures of a drawing. In this case:

Figure 1:
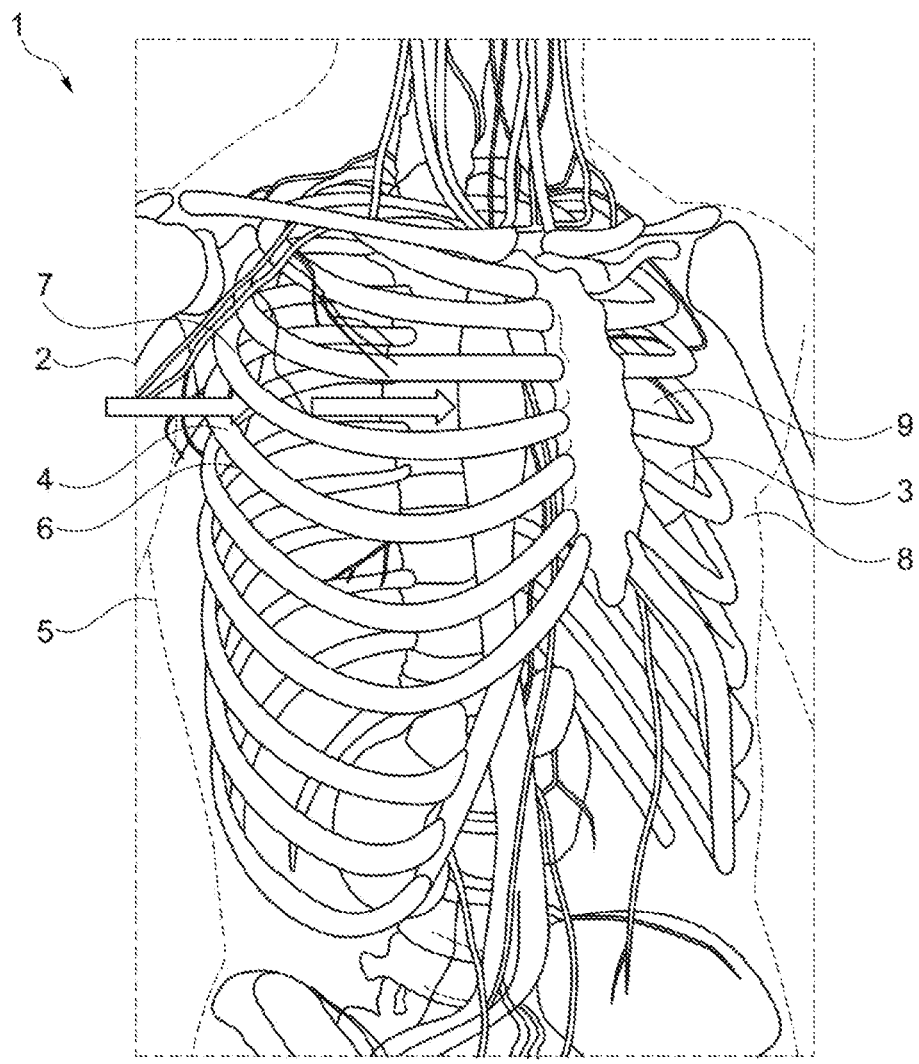
FIG. 1 shows, in a diagrammatic depiction, the thorax of a human with access to the heart from the right thoracic side.

In the figures, the same or similar elements are provided with the same reference numbers. The sizes and relative positions of the elements in the drawings are not necessarily indicated true to scale. For example, the shapes of various elements and angles are not indicated true to scale. Some of these elements are, for better depiction and for better understanding, arbitrarily shown enlarged.

The thorax 1 of a human shown in FIG. 1 in a diagrammatic depiction shows a minimally-invasive access 2 to the heart 3 for the minimally-invasive mitral valve surgery. Interventions on the mitral valve 14 of the heart 3, see FIG. 5, can be performed in a minimally-invasive manner, i.e., without use of the heart-lung machine. For example, a hybrid OR scenario in the case of an anesthetized patient can be used for mitral valve repair. Then, in the case of a collapsed right lung, multiple lateral small access openings, not shown, are made in the right ribcage 5 between the $3^{rd}$ or $4^{th}$ intercostal spaces. This intervention is carried out with the minimally-invasive technique (also called keyhole surgery) and includes, for example, trocars, self-retaining retractors, optics, an atrium top retractor, among other instruments.

The access 2 to the heart 3 is carried out, as indicated above, via a small ribcage opening 4 on the right side 5 between the $3^{rd}$ or $4^{th}$ rib space 6. The ribcage opening 4 is held open with a self-retaining retractor 7 during the operation. Additional accesses, such as, e.g., for endoscopy, not shown, are made in the thorax 1. The heart 3 is rotated around its longitudinal axis in the left thoracic space 8, so that the right half of the heart rests more on the anterior chest wall, while the left half of the heart preferably points toward the rear. An implantable device 10, in particular an annuloplasty ring 11, see FIG. 4, is provided, which when the minimally-invasive surgery is used in the beating heart 3 of a patient can be introduced via the right thoracic area 5 into an anatomical opening 9 of the heart 3 using known surgical instruments and can be anchored there.

In order to be able to penetrate into a heart 3 with the surgical instruments and implants and to correct a mitral valve insufficiency, in particular regurgitation of the blood, it is necessary to open the left atrium 12 with a small cut, an incision, and to insert a trocar. The trocar is used, e.g., to accommodate one or more catheters and as an access guide for them as well as for a device 10 that can be implanted in the left atrium 12. Analogous reference numbers from FIG. 1 are adopted in the figures below.

Figure 2:
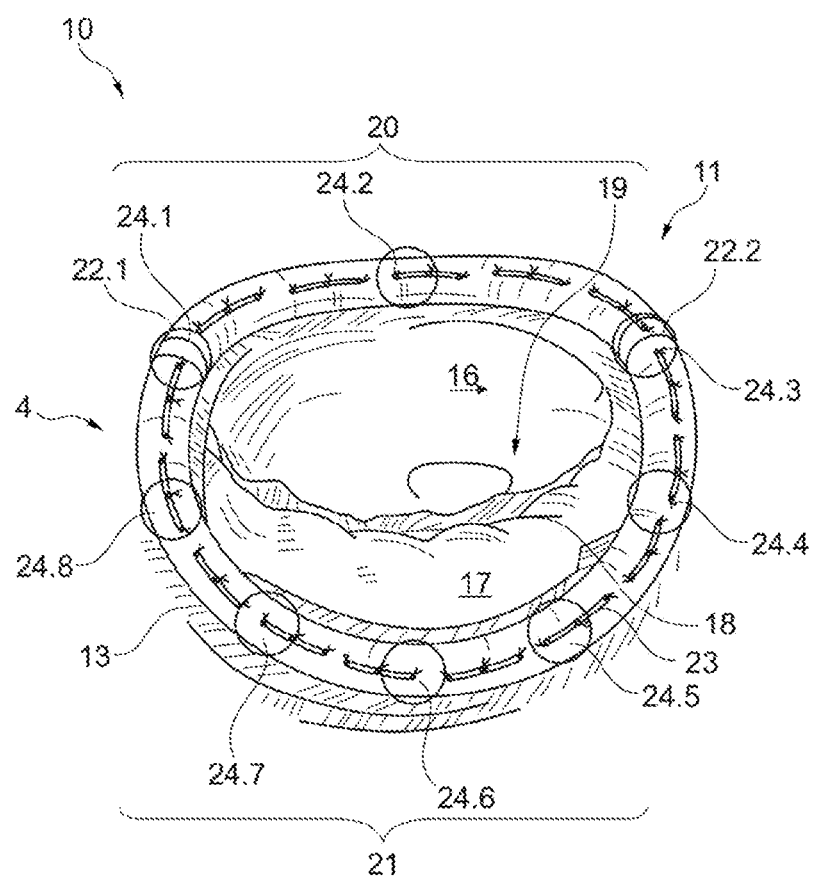
FIG. 2 shows a diagrammatic view of a top view from the state of the art of an implanted device, in particular an annuloplasty ring that is fastened to a mitral valve annulus in the left atrium of a heart.

In a diagrammatic depiction and in top view, FIG. 2 shows a device 10 that is implanted in an open heart 3, in particular an annuloplasty ring 11 from the state of the art, which is attached by a mitral valve annulus 13 in the left atrium 12 of a heart 3. The mitral valve annulus 13 has an anterior cusp 16 and a posterior cusp 17. When the annuloplasty ring 11 is implanted, the cusps 16, 17 of the mitral valve 14 are brought closer together and are supported so that they meet in the gap 18 when the valve 19 is closed. An annuloplasty ring 11 thus eliminates the problem of the functional mitral regurgitation. The annuloplasty ring 11 has an arrangement that is oval or somewhat "D-shaped" with a relatively straight anterior section 20 relative to a curved posterior section 21. Two markers 22.1, 22.2 refer to the borders between the anterior section 20 and posterior section 21. Multiple knotted thread loops 23 are typically used in order to fasten the annuloplasty ring 11 to the mitral valve annulus 13. The annuloplasty ring 11 that is shown is implanted in the open heart 3 by opening the ribcage 4.

In addition, in FIG. 2, the arrangement of the positioning 24.1-24.8 of tissue anchors 15.1-15.8 on the mitral valve annulus 13 and on the annuloplasty ring 11 is shown in dotted lines.

Information on the positioning of eight tissue anchors 15.1-15.8 is provided for the sake of clarity in FIG. 2. The possible positions 24.1-24.8 of the eight tissue anchors 15.1-15.8, which are implanted on the mitral valve annulus 13 with the minimally-invasive technique, are shown. The complete inventive device 10 with an annuloplasty ring 11, shown with six tissue anchors 15.1-15.6, is shown in FIG. 4b.

The first position 24.1 of a tissue anchor 15.1 is located at marker 22.1 on the left border between the anterior section 20 and the posterior section 21. The third position 24.3 of a tissue anchor 15.3 is located at marker 22.2 on the right border between the anterior section 20 and the posterior section 21. The second position 24.2 of a tissue anchor 15.2 is located between the first position 24.1 and the third position 24.3 in the area of the mitral valve annulus 13 of the anterior cusp 16, while the other positions 24.4 to 24.8 of the tissue anchors 15.4 to 15.8 are arranged in the area of the mitral valve annulus 13 of the posterior cusp 17. The posterior section 21 of the annuloplasty ring 11 is formed and in general follows the changed shape of the mitral valve annulus 13 in the area of the posterior cusp 17. The tissue anchors 15.4 to 15.8 are implanted in such a way that the annuloplasty ring 11 that is fastened thereto supports the shape of the mitral valve annulus 13. The annuloplasty ring 11 is not, as shown here in the state of the art of FIG. 2, attached directly to the mitral valve annulus 13 with knotted thread loops 23, but rather fastened to the tissue anchors 15.1-15.8 that are implanted on the mitral valve annulus 13, as seen from FIG. 4a. Analogous reference numbers from this FIG. 2 are adopted in the figures below.

Figure 3:
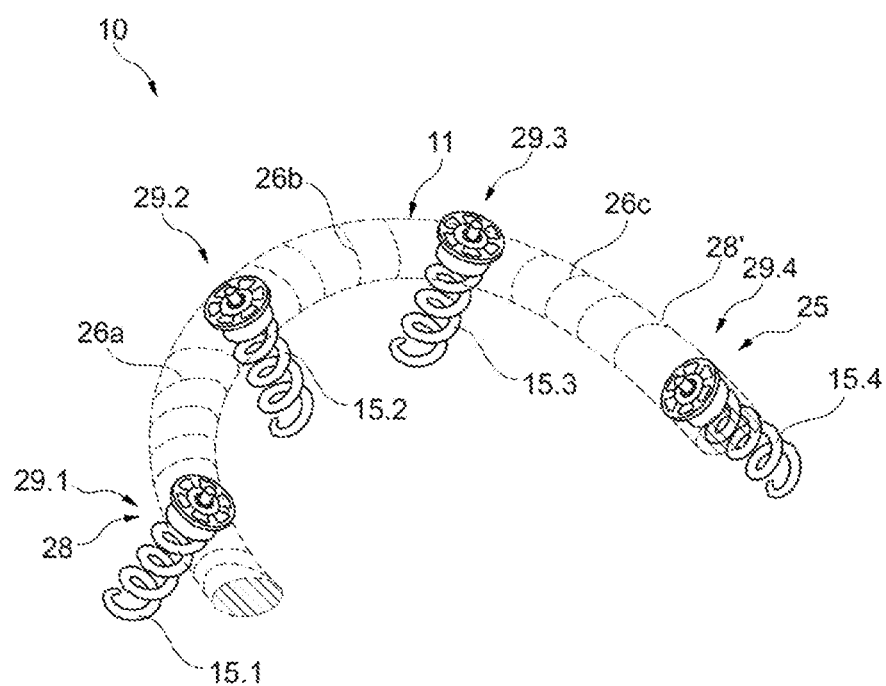
FIG. 3 shows, in a perspective depiction, another implanted device, consisting of a segmented annuloplasty ring with tissue anchors as fastening means from the state of the art.

Also, FIG. 3 shows in a perspective depiction, from the state of the art, another implanted device 10 in an unfolded configuration. The device consists of a segmented annuloplasty ring 11 with tissue anchors 15.1-15.4 as fastening means 25. The annuloplasty ring 11 has an approximately "C-shaped" configuration in order to reinforce an opening in the body tissue or to reinforce the natural valve 19. The valve 19 has the shape of a mitral valve 14; see FIG. 2. According to the embodiment, the annuloplasty ring 11 consists of three segments 26a, 26b, 26c. Between the three segments 26a, 26b, 26c and on the free ends 28, 28' of the segments 26a, 26c, in each case a tissue anchor 15.1-15.4, altogether four tissue anchors 15.1, 15.2, 15.3, 15.4, is arranged. The distance from the tissue anchors 15.1, 15.2, 15.3, 15.4 is predetermined by the length of the arc-shaped segments 26a, 26b, 26c. At the places of the tissue anchors 15.1, 15.2, 15.3, 15.4, pivot joints 29.1-29.4 are arranged in the segments 26a, 26b, 26c, which have a conical mount opening (not shown) for the tissue anchors 15.1, 15.2, 15.3, 15.4. The arc shape of the segments 26a, 26b, 26c is set in such a way that they can comprise a portion of the mitral valve annulus 13. Spiral tissue anchors 15.1, 15.2, 15.3, 15.4 are provided as fastening means 25 for the annuloplasty ring 11 on the mitral valve annulus 13. The annuloplasty ring 11 that is shown is inserted in a catheter-guided manner into the heart 3 and implanted there. Analogous reference numbers from this FIG. 3 are adopted in the figures below.

Figure 4A:
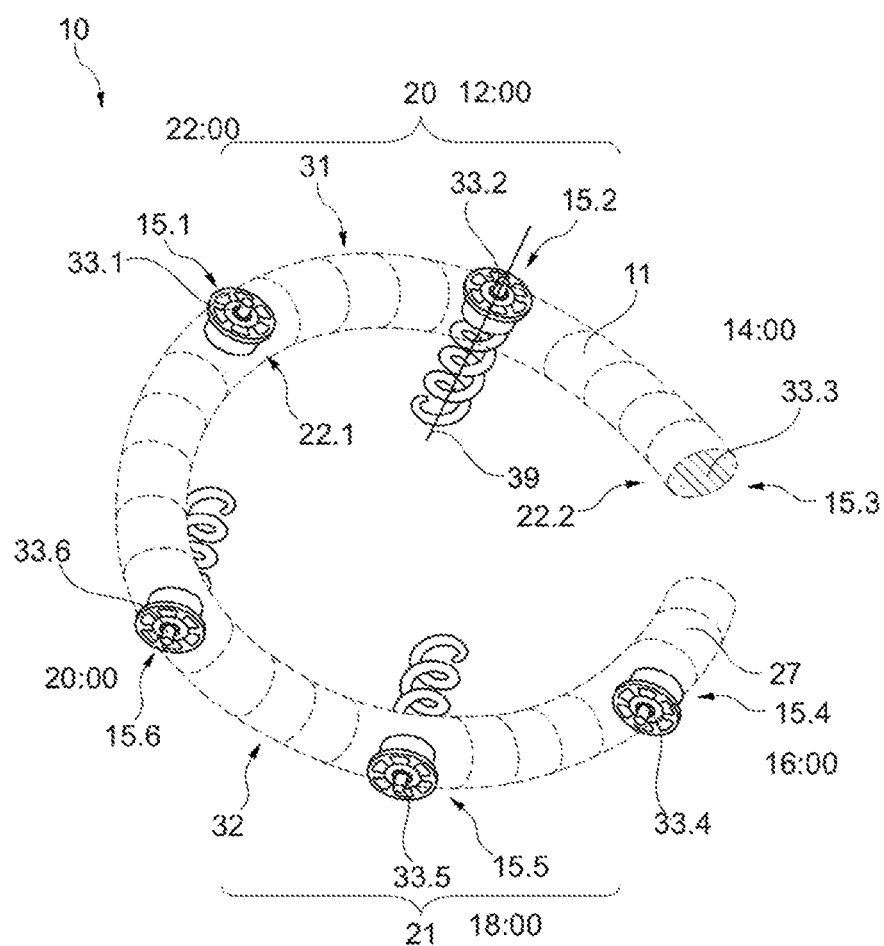
FIG. 4a shows, in a perspective depiction, an inventive implantable device that consists of an annuloplasty ring with tissue anchors as fastening means.
Figure 4B:
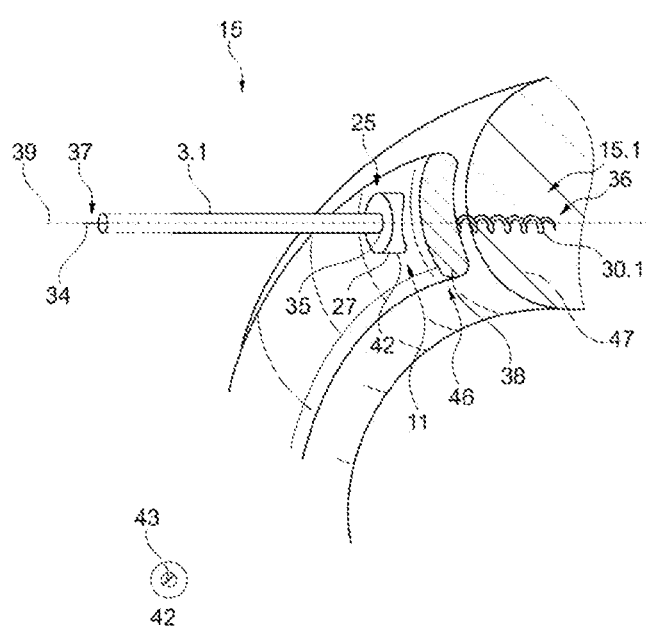
FIG. 4b shows, in a diagrammatic depiction, a cross-section from FIG. 4a with a tissue anchor and ring element in cross-section.

In a perspective depiction, FIG. 4a shows an inventive implantable device 10, consisting of an annuloplasty ring 11 with fastening means 25, whereby the fastening means 25 comprise multiple tissue anchors 15.1, 15.2, 15.3, 15.4, 15.5, 15.6. The tissue anchors 15.1, 15.2, 15.3, 15.4, 15.5, 15.6 in turn are formed from spiral coil screws 30.1-30.6, whereby other fastening means can also be possible. The depiction of the heart 3 and the cusps 16, 17 of a mitral valve 14 is omitted here for the sake of clarity. This is sufficiently evident from FIGS. 5-7. The implantation of the device 10 that is shown is carried out with use of the minimally-invasive surgery according to FIG. 1.

The inventive annuloplasty ring 11, according to this embodiment, has approximately a general circular or oval shape. In addition, the annuloplasty ring 11 has an inner layer 43 for stabilization and at least one outer layer 42, through which the at least one artificial tissue anchor thread 33 is drawn. Such an annuloplasty ring 11 comprises in cross-section a rounded ring element 27, which has a relatively straight anterior section 20 and an arc-shaped or curved posterior section 21, as also shown in FIG. 2. The anterior section 20 of an annuloplasty ring 11 is equipped with tissue anchor positions 24.1-24.3 for an anterior side 31 of a mitral valve annulus 13 of the anterior cusp 16, while the posterior section 21 is equipped with tissue anchor positions 24.4-24.6 for a posterior side 32 of a mitral valve annulus 13 of the posterior cusp 17. A tissue anchor position 24.1-24.6 in the annuloplasty ring 11 is provided with at least one tissue anchor thread 33.1-33.6 from at least one tissue anchor 15.1-15.6. The tissue anchors 15.1-15.6 are arranged around the mitral valve annulus 13. Each tissue anchor 15.1-15.6 that is implanted on the mitral valve annulus 13 is equipped with a tissue anchor thread 33.1-33.6 in order to fasten an annuloplasty ring 11 to the tissue anchors 15.1-15.6. The tissue anchor position 24.1 in the annuloplasty ring 11 lies on the same longitudinal axis 39 as the tissue anchor position 24'0.1 on the mitral valve annulus 13. That is to say, the tissue anchor position 24.1 in the annuloplasty ring 11 and the tissue anchor position 24'0.1 on the mitral valve annulus 13 are congruent, by which because of its tissue anchor position 24' 0.1 on the mitral valve annulus 13, a tissue anchor thread 33.1 of a tissue anchor 15.1 can be assigned for fastening to the same tissue anchor position 24.1 on the annuloplasty ring 11. To avoid repetitions, the above-mentioned example is representative of the other tissue anchor positions 24.2-24.6 and 24' 0.2-24' 0.6, whereby a pair of tissue anchor positions 24.2-24'0.2, 24.3-24'0.3, etc., always belongs together and is arranged on a common longitudinal axis 39.

An annuloplasty ring 11 can be fastened based on a large number of tissue anchor positions 24'0.1-24'0.6, for example six positions on the mitral valve annulus 13 and the tissue anchors 15.1-15.6 implanted therein. FIG. 2 shows eight tissue anchor positions 24.1-24.8, which are typically used to position and to fasten an annuloplasty ring 11 with its tissue anchor positions 24.1-24.8 on the tissue anchors 15.1-15.8 that are implanted in the mitral valve annulus 13.

The first position 24.1 of a tissue anchor 15.1 on the annuloplasty ring 11 is located, viewed in top view, at marker 22.1, which characterizes the left border between the anterior section 20 and the posterior section 21. The third position 24.3 of a tissue anchor 15.3 is located at marker 22.2, which marks the right border between the anterior section 20 and the posterior section 21. The second position 24.2 of a tissue anchor 15.2 is located between the first position 24.1 and the third position 24.3 in the relatively straight anterior section 20 of the annuloplasty ring 11, while the other positions 24.4 to 24.6 of the tissue anchors 15.4 to 15.6 are arranged in the area of the curved posterior section 21. The posterior section 21 of the annuloplasty ring 11 is formed and follows in general the changed shape of the mitral valve annulus 13 in the area of the posterior cusp 17. The tissue anchors 15.4 to 15.8 are implanted in such a way that the annuloplasty ring 11 that is fastened thereto supports the shape of the mitral valve annulus 13. The same applies for the tissue anchor positions 24'0.1-24'0.6 of the tissue anchors 15.1-15.6, which are arranged around the mitral valve annulus 13. The first position 24'0.1 of a tissue anchor 15.1 is located at the mitral valve annulus 13, viewed in top view, at the left border between the anterior section 20 and the posterior section 21, where the anterior cusp 16 meets the posterior cusp 17. The same also meets the third tissue anchor position 24'0.3, which lies on the right border between the anterior section 20 and the posterior section 21, where the anterior cusp 16 meets the posterior cusp 17. The second position 24'0.2 of a tissue anchor 15.2 is located between the first position 24'0.1 and the third position 24'0.3 in the area of the anterior cusp 16 of the mitral valve annulus 13, while the other positions 24'0.4 to 24'0.6 of the tissue anchors 15.4 to 15.6 are located in the area of the posterior cusp 17 of the mitral valve annulus 13.

The tissue anchor positions 24'0.1-24'0.6 and the distances between them can be indicated for the tissue anchors 15.1-15.5 on the mitral valve annulus 13, including using clock references, viewed clockwise. By way of example, the tissue anchor position 24'0.2 could be located at 12 o'clock and the two tissue anchor positions 24'0.1 and 24'0.3, which border the anterior section 20 of a mitral valve annulus 13, could be located at 2 o'clock and 10 o'clock. The tissue anchor positions 24'0.4-24'0.6 for the posterior section 21 of a mitral valve annulus 13 are located at 4 o'clock, 6 o'clock and 8 o'clock. The distances between the tissue anchors 15.1-15.6 are thus 2 hours, graphically speaking. This shows that additional tissue anchors 15, primarily in the posterior section 21 and the saddle area of the mitral valve annulus 13, could be implanted on the hour at 5 o'clock and 7 o'clock, as shown in, e.g., FIG. 2. Graphically speaking, of course, other time intervals are also possible, by which other angular distances between the tissue anchors 15 would be generated.

Starting from the geometry of a mitral valve annulus 13, the tissue anchors 15.1-15.6 can also be implanted on the mitral valve annulus 13 in such a way that an annuloplasty ring 11 can also recreate an asymmetrical opening of a mitral valve annulus 13. That is to say, the shape of an annuloplasty ring 11 can be changed based on multiple factors. By way of example, FIGS. 2 and 4a show two of the many possible embodiments. The shape of an annuloplasty ring 11 can be influenced with the implantation of additional tissue anchors 15. Also, the distances between the positions 24 of the tissue anchors 15 can be varied. The positioning of the tissue anchors 15 on the mitral valve annulus 13 therefore has special importance. An annuloplasty ring 11 that is fastened to the implanted tissue anchors 15 thus eliminates the problem of functional mitral regurgitation, since the annuloplasty ring 11, together with the implanted tissue anchors 15, exerts a tensile force on the surrounding myocardial tissue 47. In principle, annuloplasty rings 11 that are asymmetrical from the start can be used when a patient has a dysplastic anatomy on the mitral valve annulus 13. Although the material of an annuloplasty ring 11 that is used here makes possible a manual deformation, it is stiff enough to withstand another deformation on the mitral valve annulus 13 as soon as it is implanted and is subject to the normal physiological stresses.

The outer layer 42 of an annuloplasty ring 11 should be sufficiently porous and/or flexible to allow it to pass through the tissue anchor threads 33. The inner layer 43 is therefore designed to reduce the periphery of a mitral valve annulus 13. It must preserve its rear bending in the posterior section 21 against the stresses that are forwarded from the muscle tissue 47 of the heart 3 during a stroke cycle. The materials of such an inner layer 43 were previously laid out in the description by way of example. Analogous reference numbers from this FIG. 4a are adopted in the figures below.

In a diagrammatic depiction, FIG. 4b shows a cutaway X from FIG. 4a with a tissue anchor 15.1 and a ring element 27 in cross-section, by way of example of all tissue anchors 15.1-15.6. A tissue anchor 15.1 consists of, i.a., a spiral coil screw 30.1, which forms the distal end 36 of a tissue anchor 15.1, while a needle 34 is arranged at the proximal end 37 of the tissue anchor 15.1, at the free end of the tissue anchor thread 33.1. The coil screw 30.1 of the tissue anchor 15.1 is secured in a carrier disk 38, which exits from the carrier disk 38 in the direction toward the distal end 36. In addition, the carrier disk 38 is a holder for a tissue anchor thread 33.1, which exits from the carrier disk 38 to the opposite side of the coil screw 30.1. In another embodiment, the tissue anchor thread 33.1 is fastened onto the tissue anchor 15.1, and the carrier disk 38 is located on the common fastening site 46 of the thread 33.1 and the anchor 15.1. The carrier disk 38 has an attachment side 40 for the mitral valve annulus 13 and an attachment side 41 for the ring element 27. The two attachment sides 40, 41 contain two attachment surfaces I, II 44, 45. The first attachment surface I 44 serves the tissue anchor 15 as a stop when it is being screwed onto the tissue 47, while the other attachment surface II 45 serves a ring element 27 as a resting point. The diameter of the carrier disk 38 is designed in such a way that screwing a tissue anchor 15.1 too far into the myocardial tissue 47 is avoided. If all tissue anchors 15.1-15.6, see FIG. 4a, are implanted around the mitral valve annulus 13 in the myocardial tissue 47, the ring element 27 of an annuloplasty ring 11 is placed next on the carrier disk 38 of the tissue anchor 15.1-15.6. A fastening means 25 is used to fasten a ring element 27 onto the carrier disk 38 of a tissue anchor 15.1. At least one tissue anchor thread 33.1 of a tissue anchor 15.1 is fastened at least with a fastening means 25 onto the annuloplasty ring 11. The fastening means can preferably consist of a clamping means 35. The clamping means 35 is put onto a tissue anchor thread 33.1 outside of the ribcage 1. This process is carried out using the needle 34, which is guided through the opening of the clamping means 35. A surgical instrument (not shown) advances the clamping means 35 up to the ring element 27 and clamps the ring element 27 between it and the carrier disk 38. The clamping means 35 is designed in such a way that it can permanently clamp a tissue anchor thread 15.1 in its opening. For example, a clamping means 35 can also consist of two components that work against one another and exert a clamping effect on a tissue anchor thread 15.1. Preferably, the clamping element 35 can consist of a cup spring, which can be inserted relatively easily on the tissue anchor thread 33.1 into the atrium 12 and at the site of the fastening of the ring element 27 generates a clamping opposite to the feeding direction. The ring element 27, which is positioned between the clamping means 35 and the carrier disk 38 of the tissue anchor 15.1, has an inner layer 43 and an outer layer 42. The tissue anchor thread 33.1 is guided through the outer layer 42 of the ring element 27 in order not to damage the inner layer 43. The insertion of an annuloplasty ring 11 into the atrium 12 can be found in FIG. 6. After all clamping means 35 have been placed on the ring element 27, the tissue anchor threads 33.1-33.6 are severed and removed from the atrium 12 of the heart 3. Analogous reference numbers from this FIG. 4*b* are adopted in the figures below.

Figure 5:
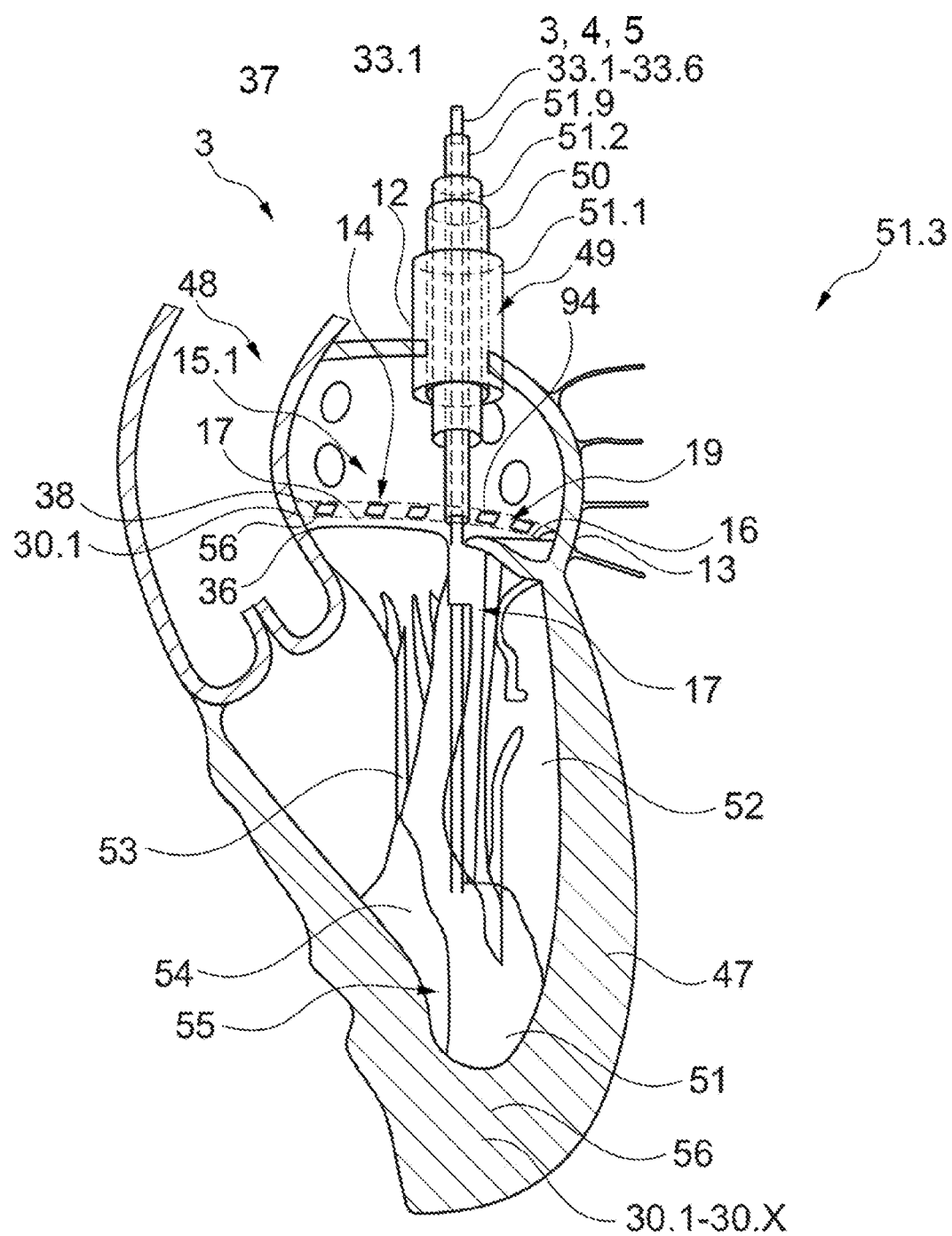
FIG. 5 shows, in a diagrammatic depiction, an implantation of the fastening means around the mitral valve annulus.

The heart 3 that is shown in FIG. 5 in a diagrammatic and basic depiction lies, according to FIG. 1, rotated around its longitudinal axis in the left thoracic space 8, so that the right half of the heart rests more on the anterior chest wall, while the left half of the heart preferably points toward the rear. A mitral valve implant, in particular an annuloplasty ring 11, is provided, which with use of minimally-invasive surgery can be introduced into the beating heart 3 of a patient via the right thorax area 5 in the left atrium 12 of the heart 3, using known surgical instruments, i.e., a trocar 50, and can be anchored there.

The left chamber of the heart 48 with the left atrium 12 and an access 49 through the heart tissue 47 in the left atrium 12 to the mitral valve 14 is therefore shown. The access 49 is carried out via the indicated trocar 50 and various surgical instruments 51.1-51.5. The various surgical instruments for mitral valve implantation with use of the minimally-invasive repair of a mitral valve annulus 13 in the beating heart 3 of the patient are cited below. A surgical instrument consists of, for example, an outer tube spacer I 51.1, in particular an access cannula with lumen for guiding an inner tube spacer II 51.2. Another surgical instrument consists of a first inner tube spacer II 51.2 with lumen for guiding and screwing-in a tissue anchor 15. Another surgical instrument consists of a second inner tube spacer III 51.3 with lumen for guiding an annuloplasty ring 11. Also, the third inner tube spacer IV 51.4 is a surgical instrument with lumen for receiving the tissue anchor threads 33.1-33.6 and for pushing an annuloplasty ring 11 out of the tube spacer III 51.3. The fourth inner tube spacer V 51.5 is also a surgical instrument with lumen for feeding a fastening means 25, in particular a clamping means 35, which is guided along a tissue anchor thread 33.1 for fastening an annuloplasty ring 11.

The left ventricle 52 is structured into an inflow and an outflow path. It is separated from the atrium 12 by the mitral valve 14. The mitral valve 14 is connected by tendinous cords (Chordae tendineae) 53 to the papillary muscles 54, which originate on the ventricle wall 55 and therefore ensure that the mitral valve 14 during its valve closure 19 and during the exertion phase (systole) of the left chamber 52 does not rebound too violently into the left atrium 12.

A mitral valve consists of four functional components: the two cusps 16, 17 (mitral valve leaflets), consisting of an anterior cusp 16 (cupis anterior), a posterior cusp 17 (cupis pasterior) and the mount of the cusps 16, 17 in the mitral valve ring 13 (mitral valve annulus). The mitral valve ring 13 consists of a muscle tissue, which is referred to in the description as mitral valve annulus 13, the tendinous cords 53 (Chordae tendineae), with which the cusps 16, 17 are fastened to move on the papillary muscles 54, and the papillary muscles 54 themselves, which protrude inward from the myocardium 47. For reconstruction of each individual component, different implants, surgical instruments and/or surgical methods are available. In this case, mitral valve regurgitation and its elimination are considered.

To this end, in the left atrium 12, tissue anchors 15.1-15.5 are inserted into the area around the mitral valve annulus 13. Since the heart 3 is shown in a sectional view, not all possible implanted tissue anchors 15.1-15.8 from FIG. 2 can be shown here, since only a portion of the periphery of a mitral valve annulus 13 is shown. The depicted tissue anchors 15.1-15.5 are representative of all implanted tissue anchors 15.1-15.5. The tissue anchors 15.1-15.5 that are implanted around the mitral valve annulus 13 are arranged at certain distances. The distances between the tissue anchors 15.1-15.5 can vary, e.g., in the saddle area of the posterior section 21 of a mitral valve annulus 13 relative to the other distances. In addition, at the distal end 36, the tissue anchors 15.1-15.5 have an anchoring element 56, whereby an anchoring element 56 consists of a corkscrew-like coil screw 30.1-30.5. The coil screws 30.1-30.5 have a distal end 36 and a proximal end 37, whereby the proximal end 37 of the coil screw 30.1-30.5 is connected to the tissue anchor threads 33.1-33.5. The use of other anchoring means for fastening an annuloplasty ring 11 is conceivable from the known state of the art. The screwed-in coil screws 30.1-30.5 are located in the myocardial tissue 47 in the area of the mitral valve annulus 13. In addition, the tissue anchors 15.1-15.5 at the proximal end 37 have a carrier disk 38 and a tissue anchor thread 33.1-33.5, which are fastened to the tissue anchors 15.1-15.5; to this end, see FIG. 4*b*. The tissue anchor threads 33.1-33.5 are guided through a sleeve 51 from the ribcage 1 for further use and are also connected to the coil screws 30.1-30.5. The further use of the tissue anchor threads 33.1-33.5 is evident from the description of FIG. 6. Analogous reference numbers from the preceding FIGS. 1-4 are adopted in this figure.

Figure 6:
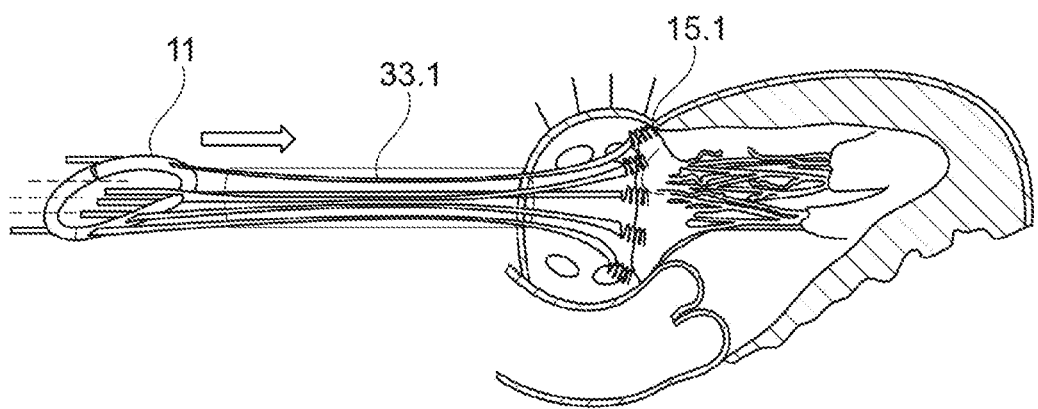
FIG. 6 shows, in a diagrammatic depiction, an annuloplasty ring in a guiding configuration.

In a diagrammatic depiction, FIG. 6 shows an annuloplasty ring 11 in a guiding configuration 57. In order to achieve a guiding configuration 57, the tissue anchor threads 33.1-33.5, which come from the tissue anchors 15.1-15.5 from the atrium 12, are guided through to predetermined positions 24.1-24.5 on the annuloplasty ring 11 outside of the ribcage 1. First, the individual tissue anchor threads 33.1-33.5, on whose free ends in each case a needle 34 is located, are guided through the fibrous ring of the outer layer 42 of an annuloplasty ring 11, which still has its starting shape 58. In order to be able to guide a tissue anchor thread 33.1-33.5 through an annuloplasty ring 11, it is necessary to know in advance which tissue anchor thread 33.1-33.5 is affected and at which point a tissue anchor thread 33.1-33.5 is to be guided through in the annuloplasty ring 11. The knowledge is necessary, since an annuloplasty ring 11 has various sections 20, 21: an anterior section 20, which is to be arranged on the front cusp 16, and a posterior section 21, which is to be arranged on the posterior cusp 17; see FIG. 2. The mitral valve annulus 13 also has these sections 20, 21. An annuloplasty ring 11 is to be placed on the mitral valve annulus 13 in such a way that their sections 20, 21 come to rest one over another. Along the sections 20, 21, around the mitral valve annulus 13, the tissue anchors 15.1-15.5 are arranged at certain distances. The distances can, however, also be irregular. The question thus arises as to from which tissue anchor 15.1-15.5 the tissue anchor thread 33.1-33.5 that lies outside of the ribcage 1 comes and at which position 24'0.1-24'0.5 this tissue anchor 15.1-15.5 is implanted on the mitral valve annulus 13. In order to be able to answer this question, the tissue anchor threads 33.1-33.5 therefore contain a corresponding identification. From the identification, it is clearly evident at which position 24'0.1-24'0.5 a tissue anchor 15.1-15.5 is positioned on the mitral valve annulus 13.

To position a tissue anchor thread 34 on the annuloplasty ring 11, it is therefore necessary to use the same position 24.1-24.5 at which the tissue anchor 15.1-15.5 is positioned on the mitral valve annulus 13. The annuloplasty ring 11 that is to be implanted therefore has, seen in top view, relative to the positioning in the tissue anchors 15.1-15.5, the same image structure as the image structure of the mitral valve annulus 13. If the first tissue anchor 15.1 is located at the first position 24'0.1, e.g., at the left transition between the curved section 21 and the straight section 20 of the mitral valve annulus 13, the tissue anchor thread 33.1 that corresponds to this tissue anchor 15.1 thus bears the identification number 1. That is to say, the identification number 1 identifies the position 24'0.1 of a tissue anchor 15.1 on the mitral valve annulus 13. However, this also means that the tissue anchor thread 33.1 of the tissue anchor 15.1 has to be guided through to the corresponding point in the annuloplasty ring 11. That is to say, to be able to place the annuloplasty ring 11 in the proper shape at the tissue anchors 15.1-15.5 on the mitral valve annulus 13, it is necessary to assign the position 24.1 on the annuloplasty ring 11 to the tissue anchor thread 33.1 with the identification number 1 and the position 24'0.1 of the tissue anchor 15.1 and at this point to guide the outer layer 42 through the tissue. The position 24.1 on the annuloplasty ring 11 also corresponds to the first position 24.1 at the left transition between the curved section 21 and the straight section 20 of the annuloplasty ring 11. The first position 24.1 on the annuloplasty ring 11 corresponds to the first position 24'0.1 of the implanted tissue anchor 15.1. The same applies for the other tissue anchor threads 33.2-33.5, which are provided by the tissue anchors 15.2-15.5 and are now drawn into the corresponding positions 24.2-24.5 through the tissue 42 of the annuloplasty ring 11. That is to say, the tissue anchor thread 33.2 of the implanted tissue anchor 15.2 has the identification number 2 and is located at the position 24'0.2 on the mitral valve annulus 13. This tissue anchor thread 33.2 is guided through to the position 24.2 of the annuloplasty ring 11, whereby the position 24'0.2 on the mitral valve annulus 13 in turn is identical to the position 24.2 on the annuloplasty ring 11, etc.

It is thus ensured that the shape of an annuloplasty ring 11 that matches the shape of a mitral valve annulus 13 can also be adapted and can be fastened onto the tissue anchors 15.1-15.5. At the positions 24.1-24.5 on the annuloplasty ring 11, at which in each case a tissue anchor thread 33.1-33.5 can be drawn through, position markers 22.1, 22.2 can, e.g., already be marked out on the annuloplasty ring 11. It is also conceivable that the positions for the tissue anchor threads 33.1-33.5 in the outer layer 42 of an annuloplasty ring 11 are already provided with a through opening for the needle 34. Through openings facilitate the threading of the tissue anchor threads 33.1-33.5 and avoid possible damage to the outer layer 42 of the ring element 27.

If an annuloplasty ring 11 is drawn onto all tissue anchor threads 33.1-33.5 that are provided by the tissue anchors 15.1-15.5, the latter is advanced onto the tissue anchor threads 33.1-33.5 up to a receiving surgical instrument 51 and compressed. In this state, the annuloplasty ring 11 has now achieved its guiding configuration 57 in order to be inserted into a sleeve 51 that is guided into the trocar 50. In this phase, the tissue anchor threads 33.1-33.5 serve as guide means for the annuloplasty ring 11. The sleeve 51, which is guided through a trocar 50, reaches up to the left atrium 12 of the heart 3. With another surgical instrument, the annuloplasty ring 11 is then moved along the tissue anchor threads 33.1-33.5 through the sleeve 51 into the atrium 12. The free ends of the tissue anchor threads 33.1-33.5 remain in addition outside of the body 1. If the annuloplasty ring 11 exits completely from the sleeve 51 and enters into the left atrium 12, it expands from its guiding configuration 57 into its original starting shape 58. The original starting shape 58 corresponds, preferably according to FIGS. 2 and 4a, to an open configuration, whereby the annuloplasty ring 11 is always still guided by the tissue anchor threads 33.1-33.5 of the tissue anchors 15.1-15.5. Along the tissue anchor threads 33.1-33.5, the annuloplasty ring 11 is now moved on the carrier disks 38, which are arranged on the ends of the tissue anchors 15.1-15.5 and placed there. As previously described, the annuloplasty ring 11 is now fastened in the proper shape to the mitral valve annulus 13, on the tissue anchors 15.1-15.5 and as shown in FIG. 4b. To fasten an annuloplasty ring 11, a tissue anchor thread 33.1-33.5 is provided with a clamping means 35, see FIG. 4b. Analogous reference numbers from the preceding FIGS. 1-5 are adopted in this figure.

Figure 7:
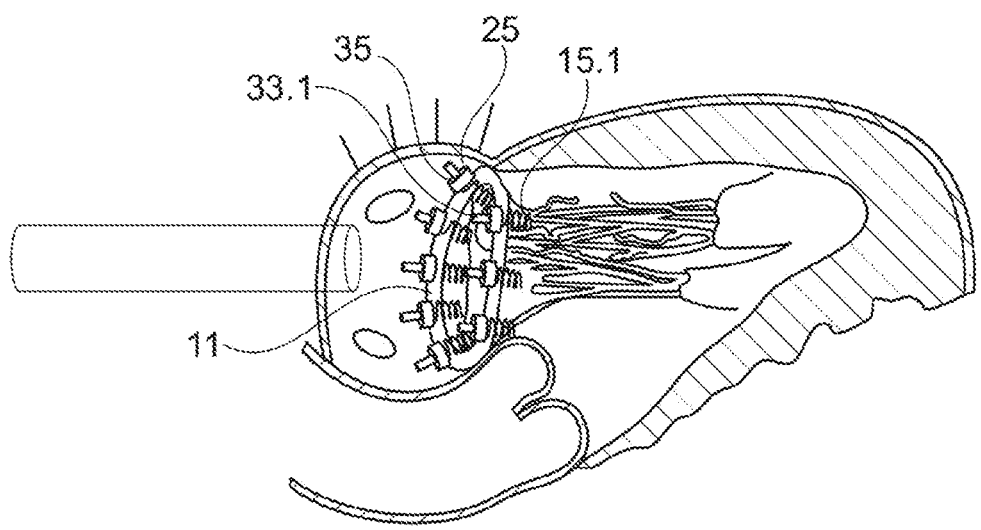
FIG. 7 shows, in a diagrammatic depiction, a device that is implanted on the mitral valve annulus.

In a diagrammatic depiction, FIG. 7 shows a device 10 that is implanted on the mitral valve annulus 13, consisting of a mitral valve implant, in particular in the form of an annuloplasty ring 11, which in principle comprises three elements. A first element is the anchoring element 56, which is designed as a tissue anchor 15 with a coil screw 30, a carrier disk 38 and a tissue anchor thread 33 and undertakes securing of the annuloplasty ring 11 in the myocardial tissue 47. The anchoring element 56 is not depicted in FIG. 7 for the sake of clarity, but it is shown in detail in FIG. 4b. The second element is the annuloplasty ring 11 as an implant that has an inner layer 43 and an outer layer 42, whereby the outer layer 42 receives the tissue anchor threads 33 that produce the connection to the tissue anchor 15. The third element forms the fastening means 25, which consists of a clamping means 35 and is guided along a tissue anchor thread 33. The clamping means 35 clamps an annuloplasty ring 11 between it and the carrier disk 38 using a tissue anchor thread 33. In conclusion, the tissue anchor threads 33.1-33.8 are still severed and, i.a., the surgical instruments 50, 51 are removed from the atrium 12, and the access 49 to the heart 3 is closed.

The tissue anchor positions 24.1-24.5 in the annuloplasty ring 11 now lie with the tissue anchor positions 24'0.1-24'0.5 on the mitral valve annulus 13 on the same longitudinal axis 39 and are thus congruent, by which a tissue anchor thread 33.1 of a tissue anchor position 24'0.1 on the mitral valve annulus 13 corresponds to the same tissue anchor position 24.1 in the annuloplasty ring 11. An annuloplasty ring 11 is thus implanted in the proper shape for eliminating mitral valve regurgitation. Analogous reference numbers from the preceding FIGS. 1-6 are adopted in this figure.

| Reference Symbol List | |
|---|---|
| 1 | Thorax |
| 2 | Access |
| 3 | Heart |
| 4 | Ribcage opening |
| 5 | Right side (of 1) |
| 6 | Rib space |
| 7 | Self-retaining retractor |
| 8 | Left thoracic space |
| 9 | Anatomical opening |
| 10 | Device |
| 11 | Annuloplasty ring |
| 12 | Atrium |
| 13 | Mitral valve annulus |
| 14 | Mitral valve |
| 15.1-15.6 | Tissue anchor |
| 16 | Anterior cusp (of 14) |
| 17 | Posterior cusp (of 14) |
| 18 | Gap (of 14) |
| 19 | Valve (of 14) |
| 20 | Anterior section (of 13) |
| 21 | Posterior section (of 13) |
| 22.1-22.2 | Marker (of 11) |
| 23 | Thread loops |
| 24.1-24.8 | Tissue anchor positions (of 11) |
| 24'.1-24'.8 | Tissue anchor positions (of 13) |
| 25 | Fastening means |
| 25a-26c | Segments |
| 27 | Ring element |
| 28 | Free end |
| 29.1-29.4 | Pivot joints |
| 30.1-30.6 | Coil screws |
| 31 | Anterior side (of 13) |
| 32 | Posterior side (of 13) |
| 33.1-33.6 | Tissue anchor thread |
| 34 | Needle (of 15, 33) |
| 35 | Clamping means |
| 36 | Distal end (of 15) |
| 37 | Proximal end (of 15) |
| 38 | Carrier disk (of 15) |
| 39 | Longitudinal axis (of 24, 24') |
| 40 | Attachment side (of 13) |
| 41 | Attachment side (of 27) |
| 42 | Outer layer (of 11, 27) |
| 43 | Inner layer (of 11, 27) |
| 44 | Attachment surface I (of 38) |
| 45 | Attachment surface II (of 38) |
| 46 | Fastening site |
| 47 | Tissue (of 3) |
| 48 | Left chamber of the heart |
| 49 | Access (to 3) |
| 50 | Trocar |
| 51 | Instrument |
| 52 | Left ventricle |
| 53 | Tendinous cords |
| 54 | Papillary muscles |
| 55 | Ventricle wall |
| 56 | Anchoring element |
| 57 | Guiding configuration |
| 58 | Starting shape |

The invention claimed is:

1. A device for implanting with minimally-invasive surgery in the beating heart of a patient for adjusting the shape and size in an anatomical opening or another lumen, which comprises an annuloplasty ring, wherein said annuloplasty ring has at least one tissue anchor;

has a guiding configuration, when the annuloplasty ring is compressed to a size that can be inserted into the left atrium, and can be deformed into an open configuration, in which the annuloplasty ring expands to its original starting shape to influence an anatomical opening and can be fastened there;

has a circular shape, which has an inner layer for stabilization and at least one outer surrounding layer, through which at least one tissue anchor thread is drawn; and has a rounded ring element, said rounded ring element having an anterior section, which is equipped with tissue anchor positions for an anterior side of a mitral valve annulus of the anterior cusp, and a posterior section, which is equipped with tissue anchor positions for a posterior side of the mitral valve annulus of the posterior cusp, which provides a tissue anchor position of the annuloplasty ring with at least one tissue anchor thread of at least one tissue anchor;

wherein at least one tissue anchor can be arranged and implanted around the mitral valve annulus and wherein each at least one tissue anchor is formed with a respective coil screw and a respective tissue anchor thread in order to position the annuloplasty ring on at least one tissue anchor;

the tissue anchor thread of each at least one tissue anchor is fastened with a fastener to the annuloplasty ring, and the fastener has a clamp which can be put onto the tissue anchor thread and is configured to permanently clamp the tissue anchor thread in an opening of the annuloplasty ring.

2. A device according to claim 1, wherein the tissue anchor positions in the annuloplasty ring and tissue anchor positions on the mitral valve annulus lie on the same longitudinal axis and thus are congruent, by which a tissue anchor thread of a tissue anchor position on the mitral valve annulus corresponds to the same tissue anchor position in the annuloplasty ring.

3. A device according to claim 1, wherein each tissue anchor further comprises a carrier disk, wherein each tissue anchor thread has a free end on which a needle is arranged, wherein the coil screw as well as the tissue anchor thread are connected to the carrier disk and the coil screw exits from the carrier disk on the side toward the distal end of the respective tissue anchor, and the tissue thread exits from the carrier disk on the opposite side toward the proximal end of the respective tissue anchor.

4. A device according to claim 3, wherein each carrier disk has a first attachment side for attachment to the mitral valve annulus and a second attachment side for attachment to the ring element.

5. A device according to claim 3, wherein the first attachment side has an attachment surface I, which serves the at least one tissue anchor when being screwed in as a stop on the tissue, while the second attachment side has an attachment surface II, which serves the ring element as an attachment.

6. A mitral valve-implant system for minimally-invasive repair of a mitral valve annulus in the beating heart of a patient, comprising the device according to claim 1 and:

an outer tube spacer I with lumen for guiding an inner tube spacer II;

a first inner tube spacer II with lumen for guiding and screwing-in each at least one tissue anchor;

a second inner tube spacer III with lumen for guiding the annuloplasty ring;

a third inner tube spacer IV with lumen for receiving each respective tissue anchor thread and for pushing the annuloplasty ring out of the tube spacer III; and a fourth inner tube spacer V with lumen for guiding each respective fastener along each respective tissue anchor thread for fastening an the annuloplasty ring.

* * * * *